United States Patent [19]

Collins

[11] Patent Number: 5,725,504
[45] Date of Patent: Mar. 10, 1998

[54] SPINAL EPIDURAL NEEDLE ASSEMBLIES

[75] Inventor: Michael Norman Collins, Folkestone, England

[73] Assignee: Smiths Industries Public Limited Company, London, England

[21] Appl. No.: 780,778

[22] Filed: Jan. 9, 1997

[30] Foreign Application Priority Data

Jan. 19, 1996 [GB] United Kingdom .................. 9601147

[51] Int. Cl.⁶ ............................................... A61M 5/178
[52] U.S. Cl. .................. 604/165; 604/117; 604/158; 604/164
[58] Field of Search .................... 604/117, 158, 604/164, 165, 167, 256, 280

[56] References Cited

U.S. PATENT DOCUMENTS

| | | | |
|---|---|---|---|
| 3,766,925 | 10/1973 | Rubricius | 128/346 |
| 4,326,516 | 4/1982 | Schultz et al. | 604/165 X |
| 4,362,156 | 12/1982 | Feller, Jr. et al. | |
| 4,429,852 | 2/1984 | Tersteegen et al. | 604/256 X |
| 4,609,370 | 9/1986 | Morrison | 604/165 |
| 4,973,312 | 11/1990 | Andrew | 604/158 |
| 5,127,626 | 7/1992 | Hilal et al. | 604/167 X |
| 5,160,323 | 11/1992 | Andrew | 604/158 |
| 5,186,712 | 2/1993 | Kelso et al. | |
| 5,255,691 | 10/1993 | Otten | 607/117 |
| 5,300,045 | 4/1994 | Plassche, Jr. | 604/158 X |
| 5,399,165 | 3/1995 | Paul, Jr. | 604/280 X |
| 5,480,389 | 1/1996 | McWha et al. | 604/165 |
| 5,556,387 | 9/1996 | Mollenauer et al. | 604/256 X |

FOREIGN PATENT DOCUMENTS

| | | |
|---|---|---|
| 0 008 451 | 3/1980 | European Pat. Off. . |
| 0 239 429 | 9/1987 | European Pat. Off. . |
| 0 402 057 | 12/1990 | European Pat. Off. . |
| 2 034 185 | 6/1980 | United Kingdom . |
| 2 063 679 | 6/1981 | United Kingdom . |

*Primary Examiner*—Sam Rimell
*Assistant Examiner*—Robert V. Racunas
*Attorney, Agent, or Firm*—Pollock, Vande Sande & Priddy

[57] ABSTRACT

A spinal epidural needle assembly has a spinal needle assembly insertable in an epidural needle assembly. The spinal needle assembly has a rotatable cam lever on its hub, which engages a resilient tongue formed from the hub. The spinal needle assembly is locked with the epidural assembly by pushing in the cam lever, which displaces the tongue inwardly into frictional contact with the epidural needle hub.

6 Claims, 1 Drawing Sheet

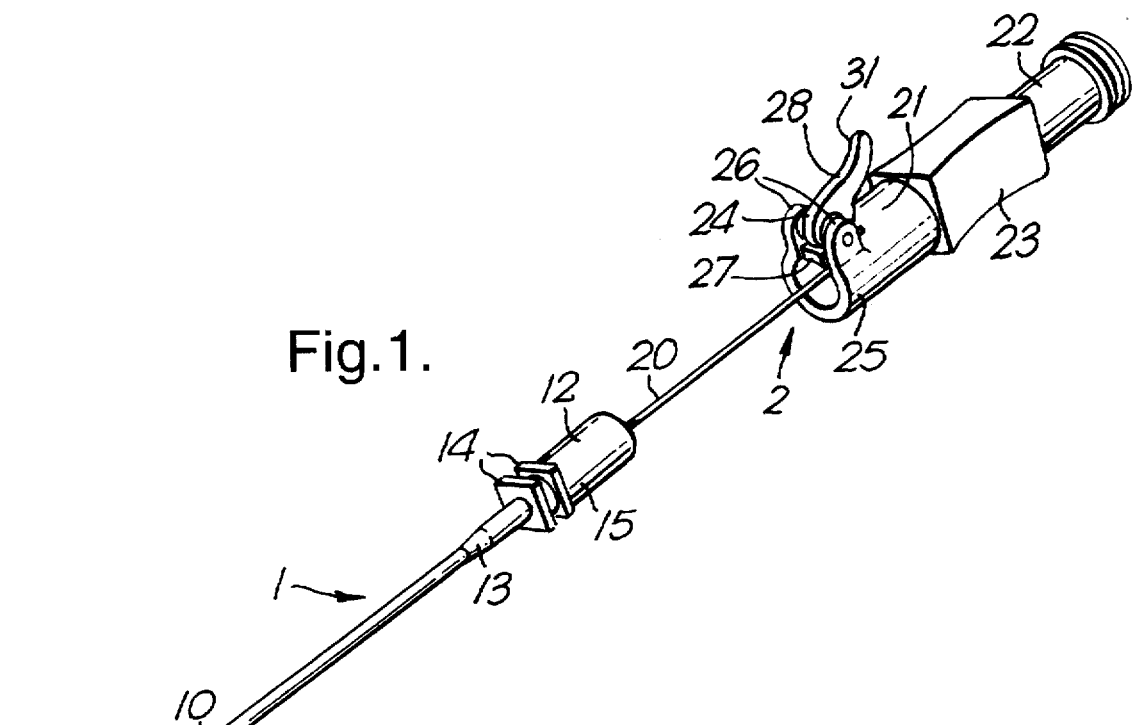
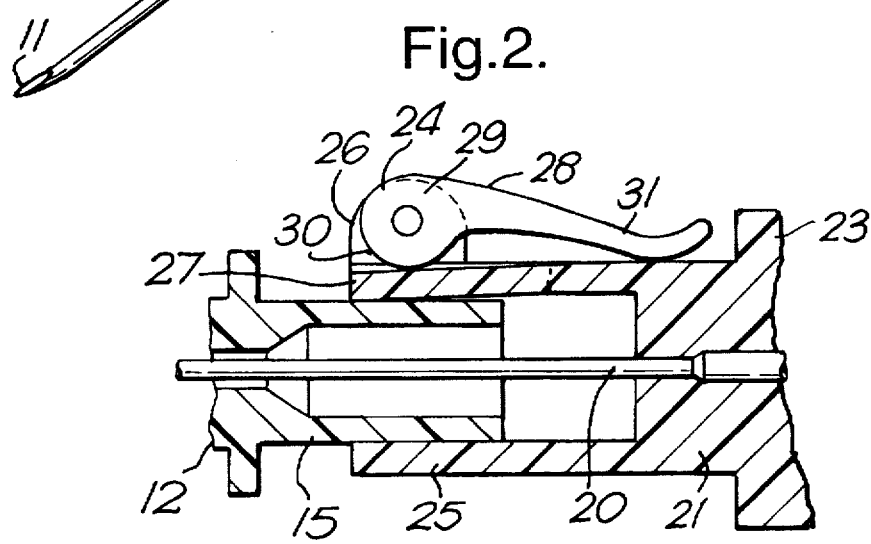

SPINAL EPIDURAL NEEDLE ASSEMBLIES

BACKGROUND OF THE INVENTION

This invention relates to spinal epidural needle assemblies.

Spinal epidural needle assemblies are used to administer anaesthetic fluid to both the spinal and epidural spaces. These assemblies comprise an epidural needle assembly and a spinal needle assembly insertable within the epidural assembly. In use, the epidural assembly is located so that its patient end is located in the epidural space. The spinal needle is pushed through the epidural needle so that it projects from its patient end and punctures the dura, entering the spinal theca. Anaesthetic fluid is then administered through the spinal needle into the spinal theca to cause almost immediate regional anaesthesia. The spinal needle is removed and an epidural catheter is pushed through the epidural needle until its tip is located within the epidural space. The epidural needle is then removed, leaving the epidural catheter in position. Anaesthetic fluid can then be given to the epidural space, as necessary. The effect of the epidural anaesthesia is less rapid but more long lasting, so the combination of the spinal and epidural anaesthesia enables effective pain control in a wide variety of situations. Examples of spinal epidural needle assemblies are described in U.S. Pat. Nos. 5,160,323, 4,973,312 and GB2124503.

Although the epidural needle is retained relatively securely by the tissue through which it passes, the spinal needle is relatively free to move longitudinally within the epidural needle. This freedom of movement is an advantage because of the very small diameter of the spinal needle and the risk that any impediment to movement could cause bending and buckling of the needle during insertion. However, the free movement of the spinal needle does have a disadvantage because it is easily displaced after positioning, such as if accidentally knocked or caught, or if the needle slips during connection of its hub to a source of anaesthetic fluid. Inadvertent displacement may cause the tip of the spinal needle to come out of the spinal theca or cause the tip to move in too far. In practice, the anaesthetist attempts to grip the spinal assembly manually by its needle or hub at the same time as holding the epidural hub, so that the spinal assembly does not slip out of position. This can be difficult to do, especially if the anaesthetist also has to connect the spinal hub to a syringe containing anaesthetic fluid. Although it would be possible to arrange the hubs on the epidural and spinal needles so that they lock or mate with one another when pushed together, this has the disadvantage that it requires the spinal needle to be fully inserted in the epidural needle.

Various proposals have been suggested for arrangements by which the spinal needle can be fixed relative to the epidural needle once the spinal needle has been correctly inserted. In Anaesthesia 1990: 45:593-594 and Acta Anaesthesiologica Scand 1994:38: 439-441, J Simsa describes a metal screw clamp attached to the epidural needle hub by which the spinal needle can be fixed in position. In EP 0564859A there is described an assembly where the spinal needle makes a bayonet-like connection with the epidural hub so that the two can be locked together, but this only enables the spinal and epidural needles to be fixed at one location. U.S. Pat. No. 540,389 and EP 0696437 describe an assembly in which the spinal needle hub has a resilient locking tab that engages between a series of teeth formed on an extension of the epidural hub. This arrangement requires the user to hold the tab in the released position while inserting the spinal needle and the space between the teeth limits the precision with which the spinal needle can be locked in position.

BRIEF SUMMARY OF THE INVENTION

It is an object of the present invention to provide an improved spinal epidural needle assembly.

According to one aspect of the present invention there is provided spinal epidural needle assembly comprising an epidural needle assembly having a needle with a hub at its machine end, and a spinal needle assembly having a needle with a hub at its machine end, the spinal needle being insertable within the epidural needle to a position in which the patient end of the spinal needle projects beyond the patient end of the epidural needle, one of said hubs having a cam member operable to clamp the two hubs together so as to prevent relative longitudinal displacement of the spinal assembly relative to the epidural assembly.

The cam member is preferably a cam lever. One hub may have a resilient member, the cam member being operable to engage the resilient member and urge it into contact with the other hub.

According to another aspect of the present invention there is provided a spinal epidural needle assembly comprising an epidural needle assembly having a needle with a hub at its machine end, and a spinal needle assembly having a needle with a hub at its machine end, the spinal needle being insertable within the epidural needle to a position in which the patient end of the spinal needle projects beyond the patient end of the epidural needle, one of said hubs having a resilient member and means operable to displace the resilient member inwardly to contact frictionally the other hub so as to prevent relative longitudinal displacement of the spinal assembly relative to the epidural assembly.

The resilient member may be a longitudinally-extending tongue. The one hub is preferably the hub of the spinal needle assembly and projects forwardly, the other hub being the hub of the epidural assembly and projecting rearwardly.

A spinal epidural needle assembly in accordance with the present invention will now be described, by way of example, with reference to the accompanying drawings.

BRIEF DESCRIPTION OF THE DRAWINGS

FIG. 1 is a perspective view of the assembly with the spinal needle assembly unclamped and partially separated from the epidural needle assembly; and FIG. 2 is a cross-sectional side elevation view of a part of the assembly with the spinal needle assembly clamped to the epidural needle assembly;

DETAILED DESCRIPTION OF THE PREFERRED EMBODIMENT

The assembly comprises an epidural needle assembly 1 and a spinal needle assembly 2 insertable within the epidural assembly.

The epidural assembly 1 comprises a conventional hollow, steel Tuohy needle 10, which is relatively stiff and is angled to one side at its patient end 11. At its machine end, the assembly has a hub 12 of polyester, or similar material, moulded onto the needle 10. The forward part 13 of the hub 12 is of relatively small diameter, not much greater than that of the needle 10, and is tapered at its end. Two square flanges 14 project radially from the hub about midway along its length and are spaced from one another by a short distance. The epidural assembly 1 may include a wing member (not shown) clipped onto the hub between the two flanges 14 so that it projects outwardly and can be used by the anaesthetist for manipulation, if required. The rear part 15 of the hub 12 is cylindrical, being about 14 mm long, of circular section, of constant diameter along its length and with a smooth outer surface. The interior of the rear part 15, as shown in FIG. 2, is hollow and tapers down to the same diameter as the bore through the needle 10 so that a spinal needle 20 and an epidural catheter (not shown) can be freely inserted into the needle.

The spinal assembly 2 comprises a conventional hollow, metal spinal needle 20 the outer diameter of which is such that it can be freely inserted into the bore of the epidural needle 10. The length of the spinal needle 20 is such that, when fully inserted into the epidural assembly 1, it projects from the patient end 11 of the epidural needle 10 by about 12 mm. At the rear, machine end of the spinal assembly 2, a hub 21 of a transparent plastics material, such as polycarbonate, is attached to the needle 20. The rear, machine end of the hub 21 is conventional, having a female luer taper coupling 22 for connection to a source of anaesthetic fluid (not shown) and a rectangular flash chamber and finger grip 23 with concave surfaces. The forward, patient end of the hub 21 differs from conventional hubs in that it provides clamping means 24. The clamping means 24 comprises a cylindrical sleeve 25 about 17 mm long and with an internal diameter substantially equal to the outer diameter of the rear part 15 of the epidural hub 12. At its forward end, the sleeve 25 has two parallel, outwardly-projecting lugs 26. Between the lugs 26, the wall of the sleeve 25 is cut along two longitudinal lines extending about half the length of the sleeve, so as to form a resilient, longitudinally-extending tongue 27, which can be displaced radially inwards. A cam lever 28 is rotatably mounted on a shaft, which extends laterally between the two lugs 26. The cam lever 28 extends longitudinally, rearwardly above the tongue 27, comprising a cam head 29, the outer periphery of which forms a cam surface 30 engaging the tongue 27, and a curved arm 31 extending rearwardly. The shape of the cam lever 28 is such that, when the arm 31 is in an outer position, as shown in FIG. 1, inclined at an angle of about 45° to the axis, the cam surface 30 does not exert a force on the tongue 27. When, however, the arm 31 is pushed in, so that it lies against the sleeve 25, the cam surface 30 bears down on the tongue 27, displacing it radially inwards by a small distance. The cam lever 28 has an over-centre action so that, it remains in the clamped, inner position until lifted out.

The epidural needle assembly 1 is used in the usual way, by introducing the tip 11 of the needle 10 into the epidural space. The epidural assembly 1 is held relatively securely in position by engagement with the tissue through which it is inserted. A stylet (not shown) is inserted in the spinal needle assembly 2, and the tip of its needle 20 is introduced through the epidural hub 12. This is done with the clamp 24 in the released position, that is, with the cam arm 31 out. The spinal assembly 2 is inserted until the tip of the needle 20 starts to emerge from the tip 11 of the epidural needle 10. In this position, the sleeve 25 embraces the rear of the rear part 15 of the epidural hub 12. The spinal assembly 2 is pushed in further until the tip of the spinal needle 20 enters the spinal theca, as indicated by the release of resistance on penetration of the dura and the flow of cerebro-spinal fluid into the flash chamber 23, after removal of the stylet. The spinal assembly 2 is now correctly positioned and is secured relative to the epidural assembly 1 simply by pushing in the cam arm 31. This pushes the tongue 27 inwardly into frictional contact with the outer surface of the epidural hub 12 and thereby effectively clamps the spinal assembly 2 to the epidural assembly 1. Because the cam surface 30 bears on the tongue 27, rather than directly on the epidural hub 12, it avoids any possible relative longitudinal movement between the spinal and epidural assemblies caused by rotation of the cam surface 30. The anaesthetist can now connect a source of anaesthetic fluid, such as a syringe, to the coupling 22 and inject the fluid into the spinal theca. This can be done without the risk of displacing the spinal assembly 2 relative to the epidural assembly 1, and hence with a minimum risk of displacing the tip of the spinal needle 20 relative to the spinal theca. When the anaesthetic fluid has been administered, the cam arm 31 is pulled outwardly to release the clamp 24 so that the spinal assembly 2 can be pulled out of the epidural assembly 1. An epidural catheter can then be inserted in the usual way.

The assembly of the present invention enables a secure and releasable clamping between the spinal and epidural assemblies 2 and 1 over a range of infinite different longitudinal positions, as determined by the length of the rear part 15 of the epidural hub 12 and the length of the sleeve 25 on the spinal hub 21. The epidural and spinal hubs 12 and 21 can be specially manufactured or they can be made by modifying conventional hubs simply by joining a circular collar onto the rear of the epidural hub, to form the rear part 15, and by joining a cylindrical sleeve 25 with the cam lever 28 onto the forward end of a conventional spinal hub.

It will be appreciated that the clamp could be provided on the epidural assembly rather than on the spinal assembly. The clamp could be a separate component fastened to the hub of the spinal or epidural needle, such as, for example, on a removable wing fastened to the epidural hub 12 between its flanges 14.

What I claim is:

1. A spinal epidural needle assembly comprising: an epidural needle assembly having an epidural needle and a hub at a machine end of said epidural needle; and a spinal needle assembly having a spinal needle and a hub at a machine end of said spinal needle, said spinal needle being insertable within said epidural needle to a position in which a patient end of said spinal needle projects beyond a patient end of said epidural needle, wherein one of said hubs has a cam member, said cam member being movable between a first rest position where said spinal needle assembly is freely movable relative to said epidural needle and a second rest position where said two hubs are clamped together so as to prevent longitudinal displacement of said spinal assembly relative to said epidural assembly.

2. An assembly according to claim 1, wherein said cam member is a cam lever.

3. An assembly according to claim 1, wherein one of said hubs has a resilient member, and wherein said cam member is operable to engage said resilient member and urge it into contact with the other of said hubs.

4. An assembly according to claim 3, wherein said resilient member is a longitudinally-extending tongue.

5. An assembly according to claim 1, wherein said one hub is the hub of said spinal needle assembly and projects forwardly, and wherein said other hub is the hub of said epidural needle assembly and projects rearwardly.

6. A spinal epidural needle assembly comprising: an epidural needle assembly having an epidural needle and a hub at a machine end of said epidural needle; and a spinal needle assembly having a spinal needle and a hub at a machine end of said spinal needle, said spinal needle being insertable within said epidural needle to a position in whcih a patient end of said spinal needle projects beyond a patient end of said eqidural needle, wherein said hub of said spinal assembly has a cam lever and a resilint tongue, said cam lever being rotatable between a first rest position where said spinal needle assembly is freely movable relative to said epidural needle, and a second rest position where the tongue is displaced inwardly into frictional contact with said hub of said epidural assembly so as to clamp said two hubs together to prevent longitudinal displacement of said spinal assembly relative to said epidural assembly.

* * * * *